United States Patent
Schick et al.

[11] Patent Number: 5,898,753
[45] Date of Patent: Apr. 27, 1999

[54] APPARATUS FOR MEASURING BONE DENSITY USING ACTIVE PIXEL SENSORS

[75] Inventors: David B. Schick, Flushing; Daniel A. Neugroschl, New York; David B. Plass, Merrick; Jonathan Singer, Dobbs Ferry, all of N.Y.

[73] Assignee: Schick Technologies, Inc., Long Island City, N.Y.

[21] Appl. No.: 08/870,376

[22] Filed: Jun. 6, 1997

[51] Int. Cl.[6] ........................................ G01T 1/24
[52] U.S. Cl. .................... 378/54; 378/98.8; 250/370.14; 250/370.09
[58] Field of Search .................. 378/54, 57, 62, 378/98.8, 98, 98.2; 250/370.09, 370.14, 580, 208

[56] References Cited

U.S. PATENT DOCUMENTS

| | | |
|---|---|---|
| 4,160,997 | 7/1979 | Schwartz . |
| 4,660,090 | 4/1987 | Hynecek . |
| 5,043,582 | 8/1991 | Cox et al. . |
| 5,079,426 | 1/1992 | Antonuk et al. . |
| 5,101,174 | 3/1992 | Hynecek . |
| 5,150,394 | 9/1992 | Karellas . |
| 5,220,170 | 6/1993 | Cox et al. . |
| 5,434,418 | 7/1995 | Schick . |
| 5,436,476 | 7/1995 | Hynecek . |
| 5,465,284 | 11/1995 | Karellas . |
| 5,471,515 | 11/1995 | Fossum et al. . |
| 5,513,252 | 4/1996 | Blaschka et al. ...................... 378/98.8 |
| 5,528,043 | 6/1996 | Spiway et al. ...................... 378/98.8 X |
| 5,572,037 | 11/1996 | Liu et al. . |
| 5,629,524 | 5/1997 | Stettner et al. ...................... 378/98.8 X |

FOREIGN PATENT DOCUMENTS

| | | |
|---|---|---|
| 0707416 | 4/1996 | European Pat. Off. . |
| 0707417 | 4/1996 | European Pat. Off. . |
| 0714038 | 5/1996 | European Pat. Off. . |
| WO9635372 | 11/1996 | WIPO . |

OTHER PUBLICATIONS

Fossum, Eric R., Active Pixel Sensors: "Are CCD's Dinosaurs?" Proc. SPIE vol. 1900, pp. 2–14, Jul., 1993.

Mendis, Sunetra, et al., "CMOS Active Pixel Image Sensor," IEEE Transactions on Electron Devices, vol. 41, No. 3, pp. 452–453, Mar., 1994.

Armstrong, L., et al., "NASA's Tiny Camera Has a Wide–Angle Future", Business Week, Mar. 6, 1995.

U.S. Patent Application No. 08/870,381, Filed Jun. 6, 1997.

*Primary Examiner*—David P. Porta
*Attorney, Agent, or Firm*—Fitzpatrick, Cella, Harper & Scinto

[57] ABSTRACT

AA method and apparatus for measuring bone density using x-ray radiation at two energy levels, and an image sensor array that comprises a plurality of CMOS active pixel sensors.

20 Claims, 7 Drawing Sheets

APPARATUS FOR MEASURING BONE DENSITY USING ACTIVE PIXEL SENSORS

BACKGROUND OF THE INVENTION

1. Field of the Invention

This invention relates to a method and apparatus for measuring the density of bones. More specifically, it relates to a method and apparatus for measuring the density of bones that are inside a body, using an image sensor that comprises an active pixel sensor array.

2. Description of the Related Art

Osteoporosis is a disease in which the calcium content of a person's bones is gradually reduced. This leads to an increased risk of fractures, particularly common in post-menopausal women. It has been estimated that approximately 40,000 American women die per year from complications due to osteoporosis.

The mineral loss from a person's bones can be estimated from a single x-ray image of a body part. A more refined existing technique for detecting the mineral loss from a person's bones is dual-energy x-ray absorptometry (DEXA). DEXA uses two x-ray images obtained using x-rays of different energy levels to compensate for the fact that bones (hard tissue) are surrounded by skin, muscle, ligaments, etc. (soft tissue) that also contribute to the x-ray image.

In a single energy systems, it is impossible to determine which portion of the overall x-ray absorption was absorbed by the soft tissue, because any point in the image may lie underneath a combination of both hard tissue and soft tissue. In contrast to single energy systems, DEXA systems use two images to obtain a set of two simultaneous equations for each pixel in the images and then solve those equations to determine the amount of x-rays that was absorbed by the bone.

For example, U.S. Pat. Nos. 5,150,394 and 5,465,284, issued to Karellas, measures bone density using x-ray radiation at two different levels of energy. In Karellas patents, x-ray radiation of two intensity levels is transmitted through a portion of the patients body to a scintillator which converts the x-rays into visible light. The visible light emitted by the scintillator is provided to a charge-coupled device (CCD), which in turn converts the visible light into an electrical signal. The Karellas system forms an image of the body from the electrical signal, and determines the density the patient's bone from the image.

The primary problem of Karellas system stems from the use of a charge-coupled device (CCD) as the image conversion device. In a CCD, packets of electrical charges are stored in one of an array of discrete locations (known as "pixels"), with the amount of charge created and stored in each pixel corresponding to the intensity of light hitting the device at that location. The amount of charge stored in each pixel is read out by the successive application of control voltages to the device, which control voltages cause the packets of charge to be moved from pixel to pixel to a single output circuit. Through this process, the output circuit produces an analog electrical signal the amplitude of which at a given point in time represents the intensity of light incident on the device at a particular correspondence spatial location.

A CCD relies in its operation on the transfer of electrons from one pixel to another, a process that is often analogized to a "bucket brigade." Accordingly, before reaching the output circuit, the transferred electrons must pass though silicon for macroscopic distances, on the order of centimeters. Because of this, the ratio of electrons successfully transferred to the number left behind per electrode, the so-called "charge transfer efficiency" (CTE), must be as close as possible to perfect (i.e., no electrons left behind) to ensure acceptable performance of the CCD.

In addition, since net CTE varies exponentially with the number of charge transfers, the requirement for transfer efficiency becomes more stringent as CCD array sizes become larger. Also, manufacturing yield may decrease as the array size increases, since CCDs are vulnerable to single point defects that can block an entire column, rendering the entire device unusable.

CCDs also require special manufacturing techniques to achieve the required high CTE. As a result of the necessity of using such techniques, CCDs are not integratable with low power CMOS circuits, the technology most appropriate for low power integration of on-chip timing and driver electronics that is required for instrument miniaturization. Moreover, since CCDs require 12–26 volts of power, devices using this technology can present something of a shock hazard.

Recently, Active Pixel Sensor (APS) technology has provided an alternative to CCDs and other sensing devices for converting light into electrical signals. This technology is shown, for example, in U.S. Pat. No. 5,471,515 to Fossum et al., and hereby incorporated by reference. In general terms, an APS array is defined as an array of light sensors having one or more active transistors associated with each pixel. The transistors, which are the pixel's "active" elements, perform gain or buffering functions.

Because each pixel has its own active element, the charges that collect below each photosite need not be transferred through a "bucket brigade" during the readout period, as in a CCD. Thus, the need for nearly perfect charge transfer is eliminated. Accordingly, an APS array does not exhibit the negative attributes associated with charge transfer across macroscopic distances required by the CCD.

Also, since APS devices can be manufactured using standard CMOS techniques, the array can operate on 5 volt power, minimizing the shock hazards of the device. An additional advantage of utilizing APS technology in x-ray applications is that CMOS wafers are made in much larger diameter than are CCD wafers which allows large sensors to be manufactured more readily.

While APS arrays have of late enjoyed a good deal of attention from those constructing light detecting devices—such as in the high definition television (HDTV) and electronic still camera fields—they have not heretofore been used to construct an x-ray detector, such as a bone density measuring device. The reasons for this are several. To begin with, an x-ray detector is generally constructed by disposing a scintillator on top of a light sensing device, so that the scintillator first converts incident x-rays into visible light, and the light sensing device in turn converts the visible light into electrical signals. Some fraction of the x-rays that enter the scintillator, however, will invariably exit the scintillator and impinge upon the light sensing device. Such unconverted x-rays would be registered by conventional APS devices, and cause spurious signals to be created, which would, in turn, result in a noisy image.

In addition, the visible light emitted by scintillators is typically in the blue-green portion of the visible spectrum. APS arrays, however, are widely believed to exhibit a very poor response to blue-green light, leading in turn to the belief that APS arrays are not suitable for use in x-ray detectors.

Also, APS devices have a higher dark signal (i.e., thermally generated currents produced by the device when not exposed to radiation) than CCDs, since the dark signal in CCDs can be significantly reduced by operating the device in the multi-phase pinned (MPP) mode. This is believed to make APS arrays less suitable as x-ray detectors than as light detectors. In particular, because scintillators emit a much smaller number of photons than are present in a light sensing environment (such as, for example, a photography environment), the dark signal is believed to be more problematic in an x-ray detector, since the dark signal, if not corrected for, will have a greater impact on the signal-to-noise ratio. This problem is of particular significance in a bone density measuring device that uses a dual-energy source of x-ray radiation, in which there is a strong incentive to keep the energy level of the x-rays very low, since the patient will be receiving two doses.

Furthermore, it has been theorized that CMOS transistors, which are the type used in constructing APS devices, are more susceptible to damage and noise generation from high frequency radiation such as x-rays than the MOS transistors used in CCDs. Still further, it has been theorized that large APS arrays will have poor manufacturing yields.

Thus, it has heretofore never been considered to use an APS array to construct bone density measuring device. There is a need, therefore, for a new type of bone density measuring device which solves the problems of CCD-based devices by exploiting APS technology, while at the same time overcoming the real and perceived drawbacks associated with using APS arrays to detect x-rays.

SUMMARY OF THE INVENTION

One object of the present invention is to provide a bone density measuring device that does not exhibit the disadvantages of CCDs discussed above.

Another object of the present invention is to provide a bone density measuring device that utilizes APS technology.

Another object of the present invention is to provide a bone density measuring device having a radiation sensor in which the active pixel sensors and circuitry for reading out the active pixel sensors are monolithically formed on a semiconductor substrate.

In accordance with one aspect at the present invention, an apparatus for measuring bone density is provided that includes radiation source that transmits x-ray radiation through a portion of a patient's body and a radiation sensor. The radiation sensor includes a scintillator that converts the radiation into a visible-light image and a sensor array that converts the visible-light image into an electrical image signal, the sensor array comprising a plurality of CMOS active pixel sensors. The apparatus also includes a processor circuit that determines the density of the patient's bone from the electrical image signal.

In accordance with another aspect of the present invention, the radiation source provides x-ray radiation at a first energy level and a second energy level. The sensor array converts the visible-light image corresponding to the first energy level x-ray radiation into a first electrical image signal and converts the visible light image corresponding to the second energy level x-ray radiation into a second electrical image signal. The processor circuit determines the density of the patient's bone form the first and second electrical image signals.

In accordance with another object of the present invention, each active pixel sensor includes a photogate electrode, a transfer gate electrode, a reset electrode and a semiconductor channel underlying the electrodes.

In accordance with yet another object of the present invention, each active pixel sensor includes a transfer gate electrode, a reset electrode and a semiconductor channel underlying the electrodes, the semiconductor channel including a photodiode formed by a p-n junction.

In accordance with yet another embodiment of the present invention, the semiconductor channel is formed in a shallow n-type well or p-type well on the top of the semiconductor substrate.

DETAILED DESCRIPTION OF THE PREFERRED EMBODIMENT

Figure 1:
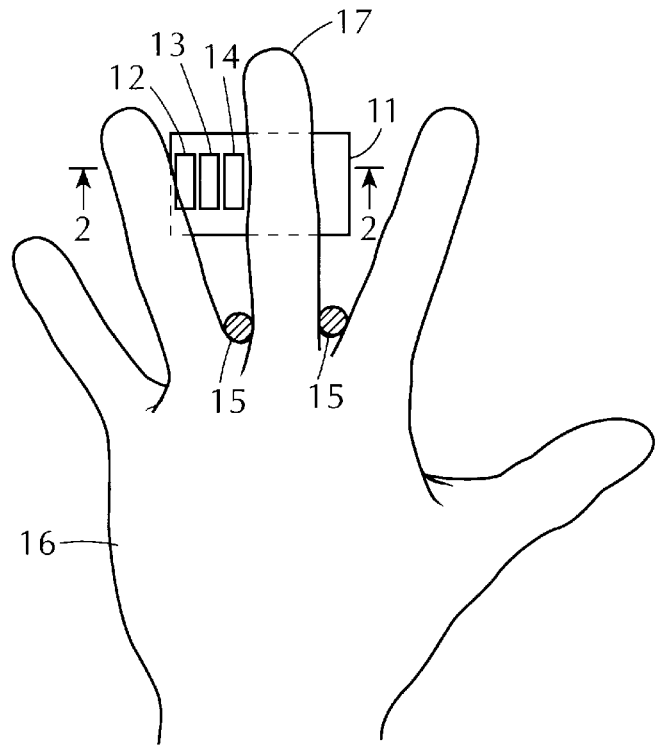
FIG. 1 is a top view of the bone density measuring device of the present invention.

FIG. 1 is a top view of the present invention being used to measure the density of a bone in the hand 16 of a patient. A radiation sensor 11 is provided that comprises a CMOS active pixel sensor (APS) array.

Before the x-ray images are obtained, the patient's finger 17 is placed over the sensor 11. A pair of guide pins 15 align the finger 17 to a desired position above the sensor 11. The preferred position is such that the middle phalange of the middle finger of the patient's non-dominant hand is located directly over the sensor 11.

A hard tissue reference 14 is also placed over the sensor. The hard tissue reference is preferably of a material with x-ray absorption characteristics similar to those of human bone. The preferred material for these wedges 12 and 14 such as aluminum. The hard tissue wedge 14 has a known thickness profile, and is used to calibrate the system.

Figure 2:
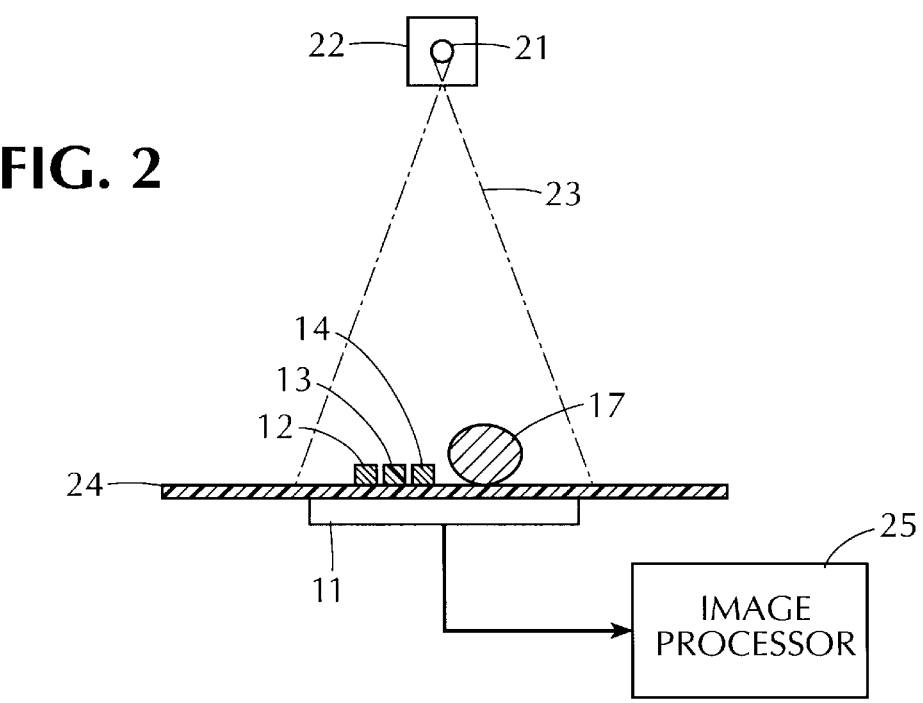
FIG. 2 is a side view of the bone density measuring device shown in FIG. 1, taken from section line 2—2.

FIG. 2 shows a side view, taken in section along the section line 2—2 of FIG. 1. Here, the sensor 11, the wedge 14 and the finger 17 from FIG. 1 can be seen in section. Also depicted is the x-ray source 21 located above the finger. The operation of the x-ray source 21 is synchronized with that of the radiation sensor 11.

An optically opaque, x-ray transparent sheet 24 ensures that the image reaching the sensor 11 is an x-ray image of the finger 17 and the wedge 14, but is not affected by ambient light. The beam of x-rays emanating from the x-ray source 21 goes through the finger 17 and the wedge 14 and strikes the sensor 11. The output from the image sensor 11 is routed to the image processor 25.

When DEXA is used, the x-ray source is excited to produce, in alternation, sprays of two different energy levels. First, the x-ray source emits a high-energy radiation that is detected by the sensor 11, producing a high-energy image that is sent to the image processor 25. Next, the x-ray source 21 emits a low-energy radiation that is also detected by the sensor 11, producing a low-energy image that is sent to the image processor 25. These two steps are preferably performed in rapid succession to minimize inter-image variations caused by movement of the finger 17 between the high-energy and low-energy exposures.

Once the high-energy image and the low-energy image are obtained, either of those images may be displayed for verification. If the displayed image is accepted by the operator, the images are then processed using known techniques to obtain a numerical measure of the patient's bone density.

When DEXA is not used, the bone density is determined from the single-energy x-ray image using known techniques.

Figure 3A:
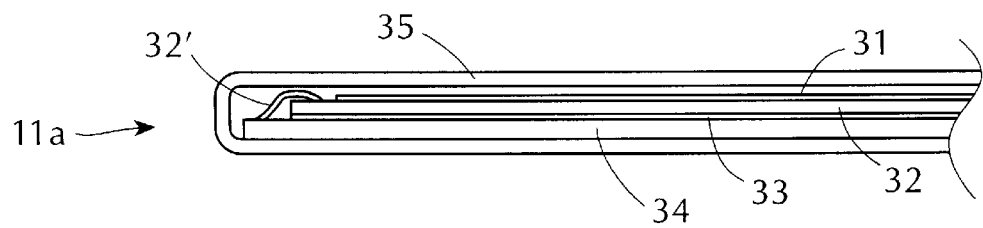
FIG. 3A is a magnified cross sectional view of one embodiment of the radiation sensor of the present invention.
Figure 3B:
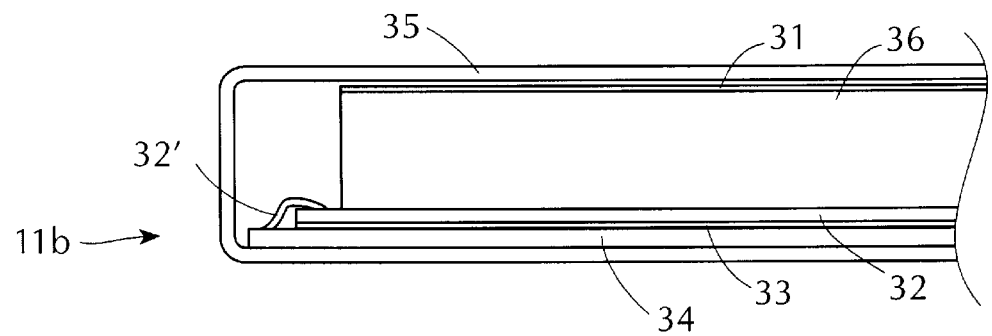
FIG. 3B is a magnified cross sectional view of another embodiment of the radiation sensor of the present invention.
Figure 3C:
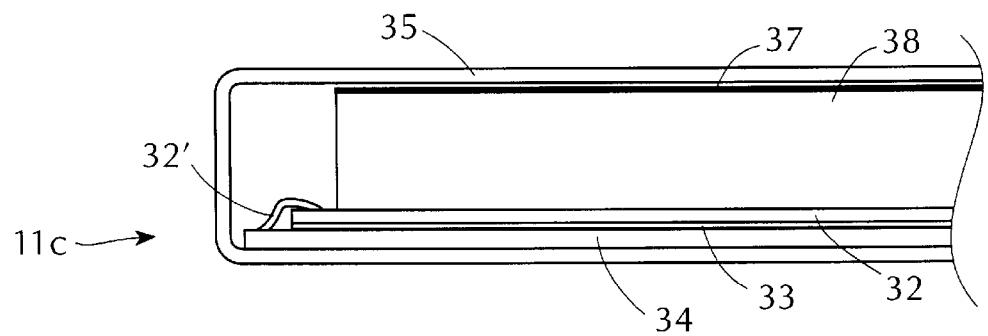
FIG. 3C is a magnified cross sectional view of yet another embodiment of the radiation sensor of the present invention.

FIGS. 3A–3C are magnified cross sectional views of three embodiments of the radiation sensor 11 of FIGS. 1 and 2. In the embodiment shown in FIG. 3A, the radiation sensor includes a scintillator 31 on top of a semiconductor 32 on top of a tungsten layer 31, all supported on a passivated ceramic substrate 34. In general terms, the scintillator 31 converts x-rays into visible light, while the semiconductor 32, in turn, converts the light into electrical signals representing the image. The tungsten layer 33 absorbs any x-rays which were not converted by the scintillator 31 to those x-rays from hitting the patient, and absorbs any backscattered radiation. The semiconductor 32 comprises a large area semiconductor image array of APS pixels and an integrated signal amplifier converted. The electrical signals produced by the semiconductor 32 are conveyed via conductive lead 32'. The conductive lead 32' may also convey electrical power and control signals to the semiconductor 32. The entire x-ray detector is enclosed in a protective plastic enclosure 35, pervious to x-ray radiation, which protects the radiation sensor from shock and enables it to be moisture resistant.

The scintillator layer 31 is interposed between the x-ray source and the semiconductor layer 32, to both protect the semiconductor from unwanted x-ray exposure and to provide conversion of the x-rays to visible light for direct detection by the semiconductor. The scintillator layer may be composed of gadolinium oxysulphate ($GD_2SO_5$) or thallium-doped cesium iodide (CsI(Tl)). Each of these materials is sensitive to x-ray photons, and efficiently converts them into visible photons in the 500–600 $\mu$m range. Other x-ray-to-light converting materials that may be used for the scintillator include cadmium telluride, cadmium sulfide, calcium tungstate ($CaWO_4$), zinc sulfide and zinc cadmium sulfide. Scintillating glass, such as for example terbium glass, or scintillating optical fibers may also be used. The scintillator 31 is positioned to be directly exposed to the x-rays which readily pass through the protective plastic enclosure 35.

In x-ray imaging, as discussed above, the x-rays are first converted into visible light by the scintillator. However, as also discussed above, the scintillator will not convert 100% of the x-rays that it receives; some x-rays will inevitably pass through the scintillator unconverted. Such unconverted x-rays cause a very large local charge which, if registered by the pixels, can create noise and dark spots in the resultant image.

One way to limit the unconverted x-rays from being registered by the APS array is to interpose a fiber optic faceplate between the scintillator 31 and the semiconductor 32. This embodiment is illustrated in FIG. 3B, which includes a fiber optic faceplate 36 between the scintillator 31 and the semiconductor 32. The fiber optic faceplate will absorb a good portion of the unconverted x-ray before they reach the APS array.

Another technique is to use scintillating fibers, which fibers absorb x-rays and emit visible light corresponding in intensity to the intensity of the x-rays. This embodiment is illustrated in FIG. 3C, which does not include a scintillator, but instead includes a scintillating fiber optic faceplate 38 on top of the semiconductor 32. In this embodiment, a reflective coating 37 is placed upon the scintillating fiber optic faceplate 38, to ensure that no visible light enters or exits from the tops of the fibers. The scintillating fibers emit a much smaller amount of unconverted x-rays than do conventional scintillating screens.

As can be readily seen from the FIGS. 3A–3C, however, using a fiber optic faceplate 36 or a scintillating fiber optic faceplate 38 results in a significantly thick sensor. Accordingly, in one embodiment of the present invention, a novel well structure is employed to prevent unconverted x-rays which do reach the APS array from contributing to the image. The novel will structure can either eliminate the need for fiber optics in the sensor, or can allow a thinner fiber optic faceplate or scintillating fiber optic faceplate to be used.

In accordance with this aspect of the invention, the photosite (e.g., the channel underlying the photogate electrode, the transfer gate electrode and the reset electrode and the floating diffusion and drain diffusion nodes) is formed in a relatively shallow n-well or a p-well. Visible light photons are relatively low in energy, and are therefore absorbed in the upper part of the semiconductor. X-ray photons, on the other hand, are relatively high in energy, and are absorbed almost exclusively deep in the semiconductor. Only the charge accumulated in the well (i.e., the charge created in response to visible light photons) is read out and contributes to the image signal; the charge accumulated below the well (i.e., the charge created in response to incident x-rays) is prevented by the well from contributing to the signal.

It should be noted that in light detection applications, such as, for example, camera applications, a shallow well structure is undesirable. This is because the longer wavelength colors of the visible light spectrum (such as red and orange) tend to be absorbed deeper in the silicon. Therefore, if an APS array having a shallow well structure were used in a camera, charge created in response to such longer wavelength light would not be read out and would not contribute to the output signal. This phenomenon does not cause a problem in the radiation sensor of the present invention, however, since the APS array need only register the shorter wave-length blue and green light emitted by the scintillator, and need not register any longer wavelength colors. The shallow well structure is therefore eminently desirable in an x-ray detector, in that it allows the light from the scintillator to contribute to the output signal, while preventing any incident x-rays from contributing.

Figure 4A:
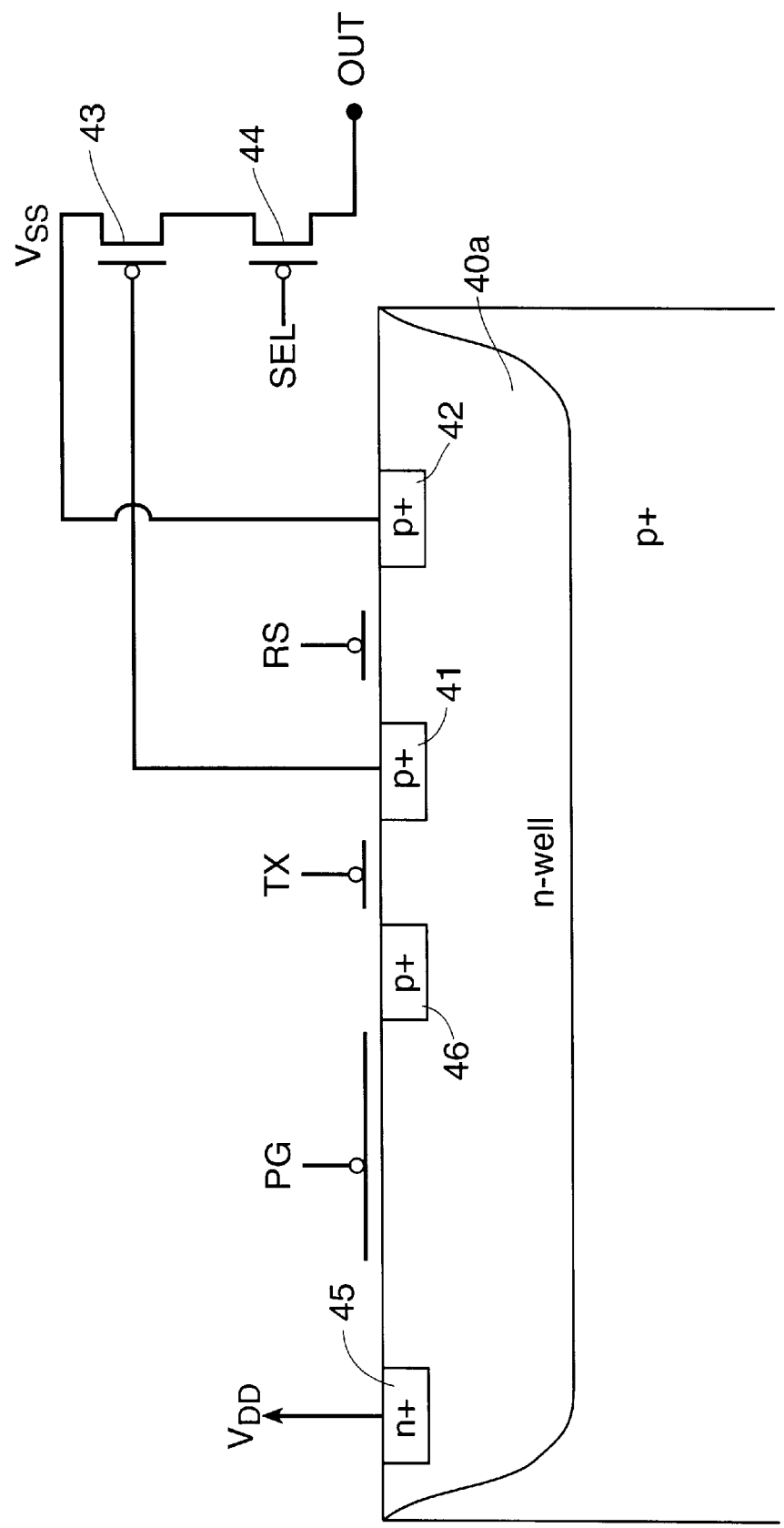
FIG. 4A is an illustration of an n-well structure according to one embodiment of the present invention.

FIG. 4A illustrates an embodiment of the novel well structure of the present invention that incorporates a photogate. In this embodiment, the photosite is formed in a thin well 40a, created by the diffusion of dopants into the semiconductor. This well should be less than $5\mu$ in thickness, and should most preferably be between $1.5\mu$ and $2\mu$. The well 40a is an n-well, formed by diffusing an n-dopant or n-dopants into a semiconductor substrate—in this case a p+ bulk silicon wafer. Since silicon is a very poor absorber of x-rays of average energy of 35 KeV, very few x-rays (less than 0.1%) will be absorbed in the top $5\mu$ of the silicon. Therefore, only the x-rays which are absorbed by the n-well (which is less than $5\mu$ in thickness) can contribute to the image. Moreover, the n-well and the remainder of the p+ silicon forms a diode structure between the active region and the substrate to inhibit migration into the active region of photogenerated charge produced in the substrate.

As can be seen in FIG. 4A, the pixel includes a relatively large photogate electrode PG, a transfer gate electrode TX, a floating diffusion node 41, a reset electrode RS and a drain diffusion node 42. Light impinging on the pixel causes charge to accumulate in the photogate (that portion of the well beneath the photogate electrode PG), with the of charge corresponding to the intensity at the light.

The floating diffusion node 41 is connected to the gate of field effect transistor (FET) 43, the drain of which is connected to drain diffusion node 42 and to a constant supply voltage $V_{SS}$. The source of FET 43 is connected to the drain of row select FET 44, which receives at its gate a row select signal SEL and in response produces at its source an output signal OUT. By the appropriate application of voltages to the electrodes and the FETs, the charge accumulated in the photogate can be read-out of the pixel, with the resultant voltage of the signal OUT being proportional to the amount of accumulated charge. And because the well 40a is so shallow, the amount of charge accumulated will be almost exclusively a function of the amount of visible light incident on the pixel, and not a function of the amount of x-rays. Accordingly, only the visible light will contribute to the output signal.

The pixel illustrated in FIG. 4A also includes an n+ plug 45 to the left of the photogate electrode PG that connects the well to a known voltage $V_{DD}$ to reverse bias the n-p+ junction formed by the well and the remainder of the silicon. Also, the pixel includes a p+ node 46 which blocks the electrons that form under the photogate electrode PG from flowing to under the transfer gate electrode TX when the transfer gate electrode TX is not properly biased (i.e., when the pixel is not being read out).

Figure 4B:
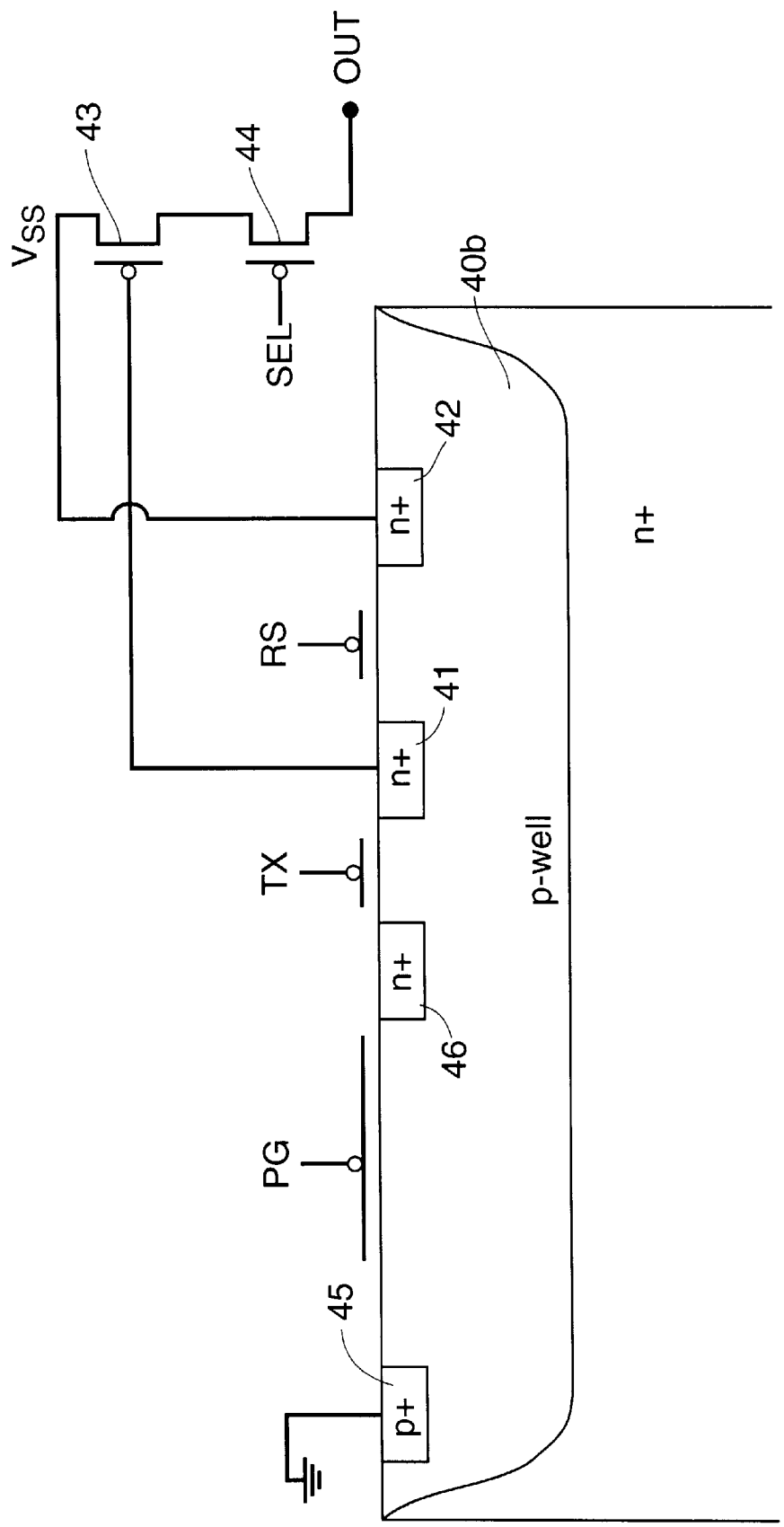
FIG. 4B is an illustration of a p-well structure according to another embodiment of the present invention.

FIG. 4B illustrates another embodiment of the present invention, in which the well 40b is a p-well, formed by diffusing a p-dopant or p-dopants into an n+ bulk silicon wafer. As can be seen, the nodes 41, 42 and 46 in this embodiment are n+ nodes, and the plug 45 is an p+ plug connected to a known voltage of ground (i.e., zero potential).

Figure 4C:
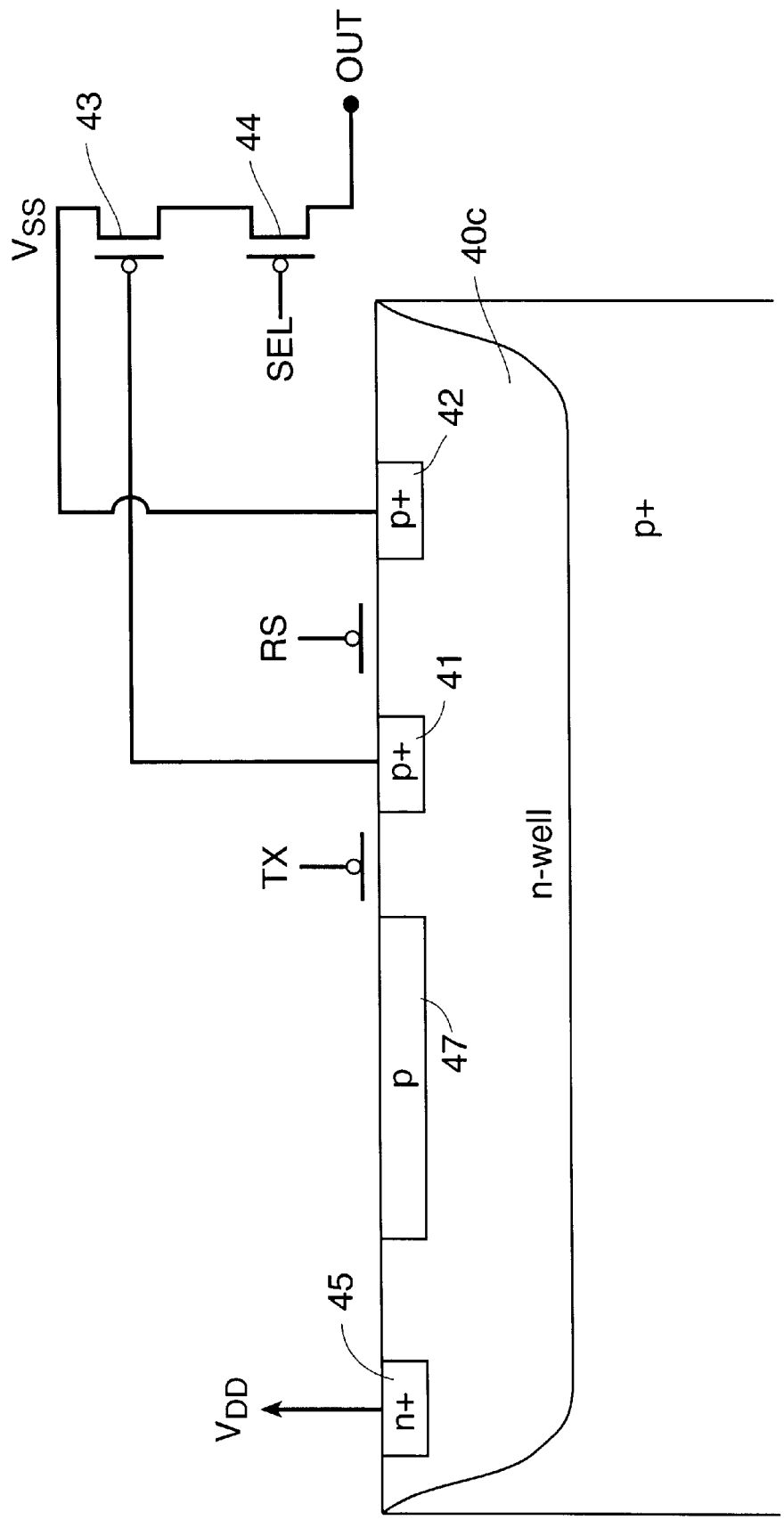
FIG. 4C is an illustration of an n-well structure according to yet another embodiment of the present invention.

FIG. 4C illustrates a photodiode embodiment of the present invention. In this embodiment, a very thin p-layer 47 is formed by the diffusion of a p-dopant or p-dopants into an n-well 40c, with the photodiode being formed by the junction between p-layer 47 and the n-well 30c. The photodiode has a junction capacitance and acts as a capacitor in operation. More particularly, each time a pixel is read out, the photodiode is charged to some known voltage. Photons absorbed in the n-well 40c (i.e., visible light photons) cause the photodiode to discharge, with the specific amount of discharge proportional to the number of photons that impinge upon the pixel. Photons absorbed below the well (i.e., x-ray photons) do not cause the photodiode to discharge. The remaining charge, therefore, represents the intensity of the light incident upon the pixel.

The pixel of the embodiment illustrated in FIG. 4C also includes a transfer gate electrode TX, a floating diffusion node 41, a reset electrode RS, a drain diffusion node 42, FETs 43 and 44 and an n+ plug 45 connected to $V_{DD}$. By the appropriate application of voltages to the electrodes and the FETs, the pixel can be read out to produce an output signal OUT proportional to the amount of charge remaining in the photodiode.

Figure 5A:
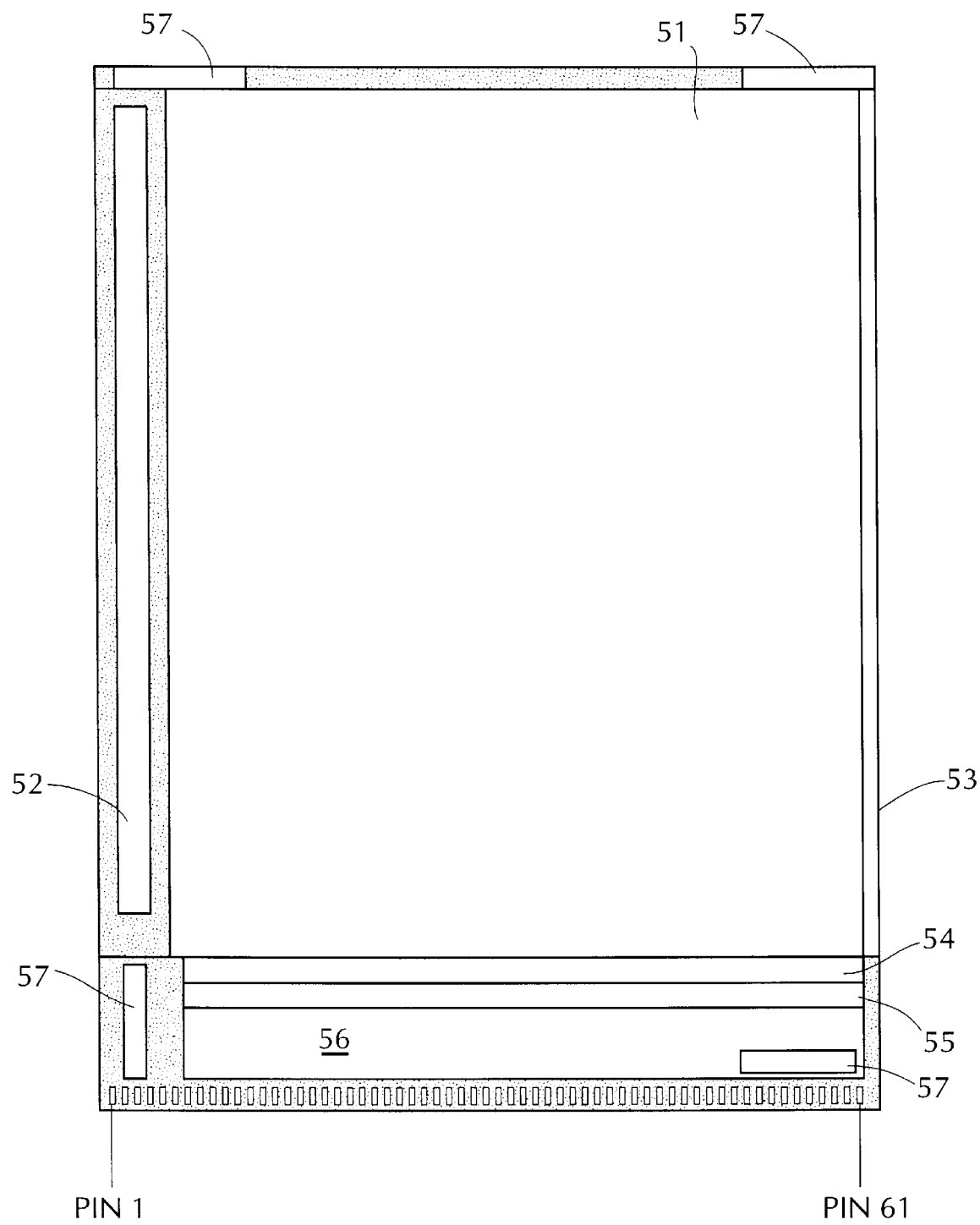
FIG. 5 is a schematic diagram of an active pixel sensor array according to one embodiment of the present invention.
Figure 5B:
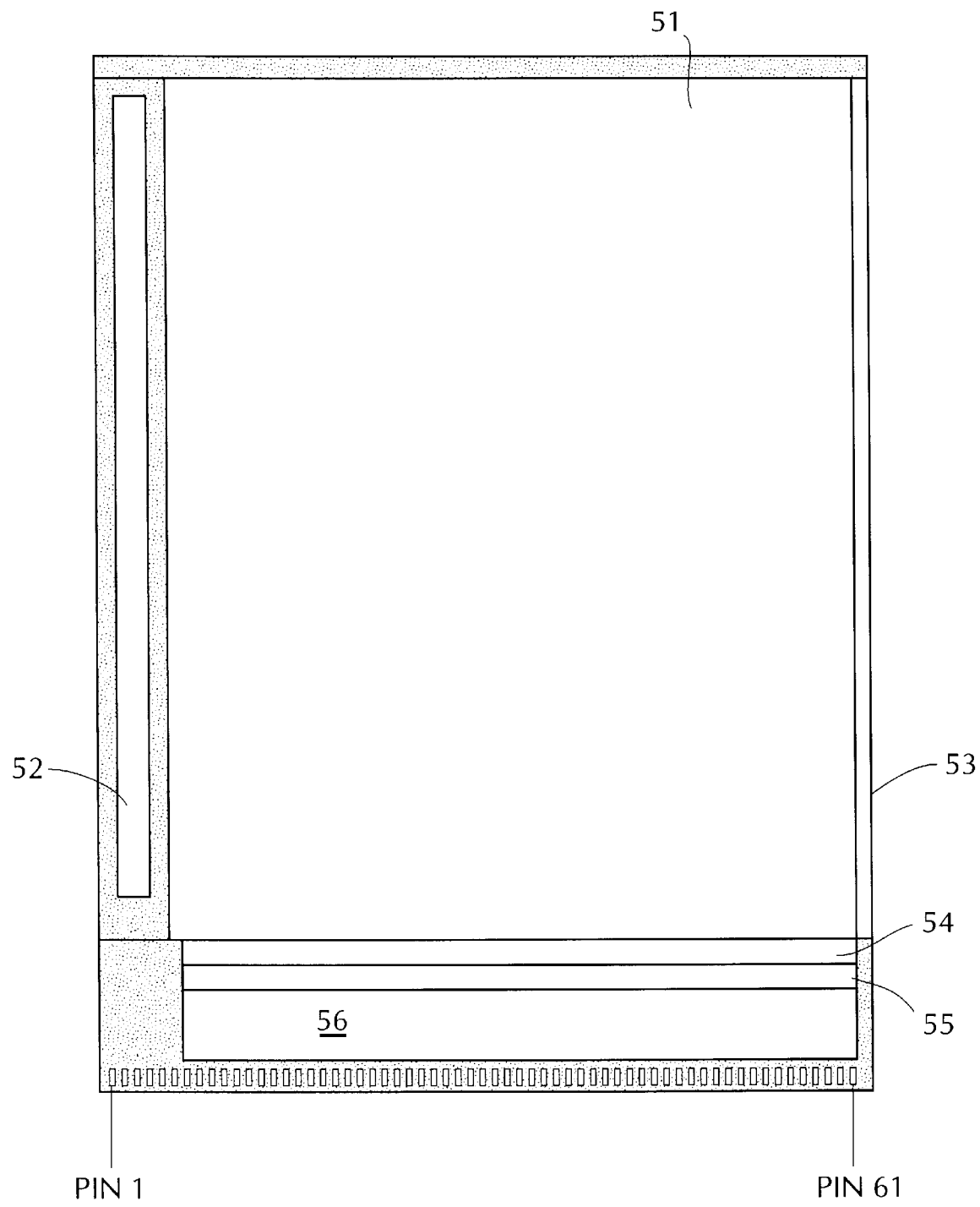

FIG. 5 illustrates an embodiments of the APS array of the present invention. The APS array 51 is self scanning, and contains on-chip all of the circuitry required to control the exposure and readout of the image. Row SR & PG drivers 52 are used to drive the rows of constituent APS pixels, APS reset drivers 53 supply reset signals to the reset electrodes of the APS pixels. Column signal chain 54, column shift registers 55, and timing and control circuitry 56 controls the reading out of the array. Pins 1 through 61 provide an input/output interface for the device. It is understood that the above description and drawings are illustrative of the present invention and detail contained therein are not to be construed as limitations on the present invention. Changes in components, procedure and structure may be made without departing from the scope of the present invention as defined in the following claims.

What is claimed is:

1. An apparatus for measuring bone density comprising:
    a radiation source that transmits x-ray radiation through a portion of a patient's body;
    a radiation sensor comprising
    (a) a scintillator that converts the x-ray radiation transmitted through the portion of the patient's body into a visible-light image and
    (b) a sensor array that converts the visible-light image into an electrical image signal, said sensor array comprising a plurality of CMOS active pixel sensors each active pixel sensor in said plurality functioning to detect photons incident upon it; and
    a processor circuit that determines a density of the patient's bone from the electrical image signal.

2. An apparatus according to claim 1, wherein
    the radiation source provides x-ray radiation at a first energy level and a second energy level;
    the sensor array converts a visible-light image corresponding to the first energy level x-ray radiation into a first electrical image signal and converts a visible-light image corresponding to the second energy-level x-ray radiation into a second electrical image signal; and
    the processor circuit determines a density of the patient's bone from the first electrical image signal and the second electrical image signal.

3. An apparatus according to claim 2, wherein said active pixel sensors and circuitry for reading out said active pixel sensors are monolithically formed on a semiconductor substrate.

4. An apparatus according to claim 3, wherein each active pixel sensor in said plurality comprises:
    a photogate electrode;
    a transfer gate electrode;
    a reset electrode; and
    a semiconductor channel underlying said photogate electrode, said transfer gate electrode and said reset electrode.

5. An apparatus according to claim 4, wherein said semiconductor channel is formed in a shallow well on the top of said semiconductor substrate.

6. An apparatus according to claim 5, wherein the shallow well is an n-type well.

7. An apparatus according to claim 5, wherein the shallow well is a p-type well.

8. An apparatus according to claim 5, wherein the shallow well is less than $5\mu$ in thickness.

9. An apparatus according to claim 8, wherein the shallow well is between $1.5\mu$ and $2\mu$ in thickness.

10. An apparatus according to claim 3, wherein each active pixel sensor in said plurality comprises:
    a transfer gate electrode;

a reset electrode; and a semiconductor channel underlying said transfer gate electrode and said reset electrode, and including a photodiode formed by a p-n junction.

11. An apparatus according to claim 10, wherein said semiconductor channel is formed in a shallow well on the top of said semiconductor substrate.

12. An apparatus according to claim 11, wherein the shallow well is an n-type well.

13. An apparatus according to claim 11, wherein the shallow well is less than $5\mu$ in thickness.

14. An apparatus according to claim 13, wherein the shallow well is between $1.5\mu$ and $2\mu$ in thickness.

15. An apparatus according to claim 2, wherein said scintillator comprises a material selected from the group consisting of gadolinium oxysulphate, thallium-doped cesium iodide, cadmium telluride, cadmium sulfide, calcium tungstate, zinc sulfide and zinc cadmium sulfide.

16. An apparatus according to claim 2, wherein said scintillator comprises scintillating glass.

17. An apparatus according to claim 2, wherein said scintillator comprises scintillating optical fibers.

18. An apparatus according to claim 2, further comprising a fiber optic faceplate between said scintillator and said sensor array.

19. An apparatus for measuring bone density comprising:

means for transmitting x-ray portion of a patient's portion of a patient's body;

means for converting the x-ray radiation transmitted through the portion of the patient's body into visible-light image;

means for converting the visible-light image into an electrical image signal, said conversion means comprising a plurality of CMOS active pixel sensors, each active pixel sensor in said plurality functioning to detect photons incident upon it; and means for determining a density of the patient's bone from the electrical image signal.

20. An apparatus for measuring bone density comprising:

means for transmitting x-ray radiation at a first energy level and a second energy level through a portion of a patient's body;

means for converting the first energy level x-ray radiation into a first visible-light image and the second energy level radiation into a second visible-light image;

means for converting the first visible-light image into an first electrical image signal and the second visible-light image into a second electrical image signal, said conversion means comprising a plurality of CMOS active pixel sensors, each active pixel sensor in said plurality functioning to detect photons incident upon it; and means for determining a density of the patient's bone from the first electrical image signal and the second electrical image signal.

* * * * *